(12) United States Patent
Wu et al.

(10) Patent No.: US 7,211,574 B2
(45) Date of Patent: May 1, 2007

(54) SELECTIVE D1/D5 RECEPTOR ANTAGONISTS FOR THE TREATMENT OF OBESITY AND CNS DISORDERS

(75) Inventors: Wen-Lian Wu, Edison, NJ (US); Duane A. Burnett, Bernardsville, NJ (US); William J. Greenlee, Teaneck, NJ (US); Thavalakulamgara K. Sasikumar, Westfield, NJ (US)

(73) Assignee: Schering Corporation, Kenilworth, NJ (US)

(*) Notice: Subject to any disclaimer, the term of this patent is extended or adjusted under 35 U.S.C. 154(b) by 267 days.

(21) Appl. No.: 10/649,495

(22) Filed: Aug. 27, 2003

(65) Prior Publication Data

US 2004/0058906 A1    Mar. 25, 2004

Related U.S. Application Data

(60) Provisional application No. 60/406,856, filed on Aug. 29, 2002.

(51) Int. Cl.
*A61K 31/55* (2006.01)
*A61P 25/30* (2006.01)
*C07D 487/00* (2006.01)

(52) U.S. Cl. .................... 514/215; 540/578
(58) Field of Classification Search ............... 514/215; 540/578
See application file for complete search history.

(56) References Cited

FOREIGN PATENT DOCUMENTS

| EP | 0230270 A | 7/1987 |
|---|---|---|
| EP | 0351733 A | 1/1990 |
| WO | WO 03/006466 | 1/2003 |

OTHER PUBLICATIONS

Hollander, et al., J. Clin. Psychiatry 57 (Suppl. 8), pp.3-6 (1996).
Phillips, J. Clin. Psychiatry 57 (Suppl. 8), pp 61-64 (1996).
Merck Index, 15th Edition (1987), p. 2280-2281.
Christenson, Gary; O'Sullivan Richard, Trichotillomania: Rational treatment options, CNS Drugs (1996), 6(1), 23-34.
Tukel R; Keser V; Karali Nt; Olgun To; Calikusu C., Comparison of clinical characteristics in trichotillomania and obsessive-compulsive disorder, Journal of Anxiety Disorders (Sep.-Oct. 2001), 15(5), 433-441.
Du Toit P L; van Kradenburg J; Niehaus D J; Stein D J, Characteristics and phenomenology of hair-pulling: an exploration of subtypes, Comprehensive Psychiatry (May-Jun. 2001), 42(3), 247-256.
International Search Report for PCT/US 03/26878 (CN01622), international filing date Aug. 27, 2003, 5 pages.

*Primary Examiner*—Brenda Coleman
(74) *Attorney, Agent, or Firm*—William Y. Lee

(57) ABSTRACT

The present invention provides compounds, which, are novel antagonists for $D_1/D_5$ receptors as well as methods for preparing such compounds. In another embodiment, the invention provides pharmaceutical compositions comprising such $D_1/D_5$ receptor antagonists as well as methods of using them to treat CNS disorders, obesity, metabolic disorders, eating disorders such as hyperphagia, and diabetes.

16 Claims, No Drawings

SELECTIVE D1/D5 RECEPTOR ANTAGONISTS FOR THE TREATMENT OF OBESITY AND CNS DISORDERS

CROSS REFERENCE TO RELATED APPLICATIONS

This application claims the benefit of U.S. Provisional Application 60/406,856 filed on Aug. 29, 2002.

FIELD OF THE INVENTION

The present invention relates to bioisostere heterocycles useful as $D_1/D_5$ receptor antagonists, pharmaceutical compositions containing the compounds, and methods of treatment using the compounds and compositions to treat obesity, metabolic disorders and CNS disorders.

BACKGROUND OF THE INVENTION

Considerable research has been directed at obesity, nicotine addiction and substance abuse. The cost to society is very high from the health costs associated with obesity and addictions. Accordingly, it would be desirable to provide a substance, which would suppress cravings for food, and other substances in a predisposed patient.

Substances, which are administered to reduce craving should not produce significant physiological effects, such as stimulation of mood or elevate blood pressure or heart rate. This could result in the substitution of one abused substance for another. Compounds which dampen the desire for the abused substance, also should not exacerbate the physiological symptoms of the abused substance in the event the individual relapses and takes the abused substance. Substances administered to reduce craving also should not produce significant adverse effects, such as dysphoria, restlessness or stiffness.

In addition to obesity and the disorders listed above, there is a strong need for drug therapy which can effectively treat, ameliorate and prevent central nervous system (CNS) disorders such as obsessive compulsive disorder, somatoform disorders, dissociative disorders, eating disorders, impulse control disorders, trichotillomania and autism. Obsessive-compulsive disorder ("OCD"), recognized to be among the most common of all psychiatric disorders, occurs in 2 to 3% of the U.S. population. OCD is characterized by anxiety-provoking and intrusive thoughts (e.g., fear of contamination and germs, doubt and uncertainty about future harm, need for symmetry, etc.), which lead to ritualistic and/or irrational behavior (e.g., constant checking, washing, touching, counting, etc.). See Hollander, et al., J. Clin. Psychiatry 57 (Suppl. 8), pp. 3–6 (1996).

Somatoform disorders (e.g., body dysmorphic disorder and hypochondriasis) are characterized by abnormal preoccupation with one's appearance or physical condition. For example, body dysmorphic disorder is a preoccupation with an imagined or slight defect in appearance. Many sufferers of body dysmorphic disorder are severely debilitated by their abnormal preoccupation, with significant impairment in social, occupational, or other important aspects of daily life. See Phillips, J. Clin. Psychiatry 57 (suppl. 8), pp. 61–64 (1996). Hypochondriasis is characterized by a persistent conviction that one is, or is likely to become ill. Many hypochondriacs are unable to work or engage in ordinary activities due to their preoccupation with illness.

Dissociative disorders (e.g., depersonalization) are characterized by sudden temporary alterations in identity, memory, or consciousness, segregating normally integrated memories or parts of the personality from the dominant identity of the individual. Depersonalization disorder, which is a dissociative disorder, is characterized by one or more episodes of depersonalization (feelings of unreality and strangeness in one's perception of the self or one's body image).

Eating disorders (e.g., anorexia nervosa, bulimia, and binge eating) are characterized by abnormal compulsions to avoid eating or uncontrollable impulses to consume abnormally large amounts of food. These disorders affect not only the social well-being, but also the physical well-being of sufferers.

Impulse control disorders (e.g., pathological gambling, compulsive buying, sexual compulsions and kleptomania) are characterized by a preoccupation with, and an inability to refrain from repeatedly engaging in various behaviors that are either socially unacceptable, or abnormally excessive by societal norms.

Trichotillomania is a habitual hair pulling that usually appears in children. See Merck Index, 15$^{th}$ Edition (1987); Christenson, Gary; O'Sullivan, Richard, Trichotillomania: Rational treatment options, CNS Drugs (1996), 6(1), 23–34; Tukel R; Keser V; Karali N T; Olgun T O; Calikusu C., Comparison of clinical characteristics in trichotillomania and obsessive-compulsive disorder, JOURNAL OF ANXIETY DISORDERS (2001 September–October), 15(5), 433–41; du Toit P L; van Kradenburg J; Niehaus D J; Stein D J, Characteristics and phenomenology of hair-pulling: an exploration of subtypes, COMPREHENSIVE PSYCHIATRY (2001 May–June), 42(3), 247–56.

Autism is a disorder characterized by a preoccupation with one's own self and a severe impairment of the ability to perceive or react to outside stimuli in a normal fashion. Many autistics are incapable of even communicating with others.

In view of the tragic and debilitating effects of these disorders, there is a strong need for a drug therapy which can effectively treat such disorders.

SUMMARY OF THE INVENTION

In its many embodiments, the present invention provides a novel class of bioisostere heterocycles as $D_1/D_5$ receptor antagonists, methods of preparing such compounds, pharmaceutical compositions comprising one or more such compounds, methods of preparing pharmaceutical compositions or formulations comprising one or more such compounds, and methods of treatment, prevention, inhibition or amelioration of obesity, metabolic disorders, CNS disorders or one or more diseases associated with obesity using such compounds or pharmaceutical compositions.

In one aspect, the present application provides a compound, or pharmaceutically acceptable salts or solvates of said compound, said compound having the general structure shown in formula I:

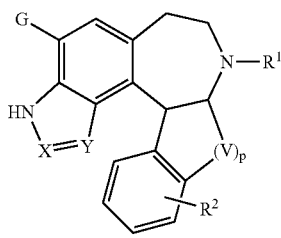

formula I wherein
p is 0, 1 or 2 and when p is 0, the carbons to which (V)$_p$ is shown connected are not linked to each other but are linked to hydrogen;

G is hydrogen, halo, alkyl, alkylthio, nitro, nitrile, hydroxy, alkoxy, alkylsulfinyl, alkylsulfonyl, trifluoromethyl or trifluromethoxy;

V is —CH$_2$—;

X is selected from the group consisting of CH, C(alkyl), CCF$_3$ and N;

Y is selected from the group consisting of CH, C(alkyl) and N;

$R^1$ is hydrogen, alkyl, allyl, cycloalkyl or cycloalkyl (alkyl);

$R^2$ is hydrogen or 1 to 4 substituents which can be the same or different, each $R^2$ being independently selected from the group consisting of halogen, alkyl, alkylthio, alkylsulfonyl, hydroxy, alkoxy, trifluoromethyl, trifluoromethoxy, aryl, —CH=O, —NO$_2$, —NR$^{11}$R$^{12}$, CN, R$^{10}$-substituted aryl, heteroaryl, —C(O)OR$^8$, —C(O)NR$^3$R$^4$, —S(O)$_2$NR$^3$R$^4$, —C(R$^7$R$^8$)NR$^5$R$^6$, —C(R$^7$)=NOR$^4$ and —C(R$^7$R$^8$)OR$^6$;

$R^3$ is aryl, R$^{10}$-substituted aryl, arylalkyl, heteroaryl, alkyl or hydrogen;

$R^4$ is aryl, R$^{10}$-substituted aryl, heteroaryl, alkyl or hydrogen, or R$^3$, R$^4$ and N of —NR$^3$R$^4$ together can be joined together to form a ring selected from the group consisting of azetidine, R$^8$-substituted azetidine, pyrrolidine, R$^8$-substituted pyrrolidine, piperidine, R$^8$-substituted piperidine, piperazine, R$^8$-substituted piperazine, morpholine and R$^8$-substituted morpholine;

$R^5$ is alkyl, arylalkyl, —C(O)NR$^3$R$^4$, —S(O)$_2$NR$^3$R$^4$, —S(O)$_2$R$^8$, —C(O)R$^8$, —C(O)OR$^8$ or —R$^9$O-alkyl;

$R^6$ is hydrogen, alkyl, aryl, R$^{10}$-substituted aryl, heteroaryl or arylalkyl, or R$^5$, R$^6$ and N in —NR$^5$R$^6$ together can be joined together to form a ring selected from the group consisting of azetidine, R$^8$-substituted azetidine, pyrrolidine, R$^8$-substituted pyrrolidine, piperidine, R$^8$-substituted piperidine, piperazine, R$^8$-substituted piperazine, morpholine and R$^8$-substituted morpholine;

$R^7$ is hydrogen, alkyl, aryl or arylalkyl;

$R^8$ is hydrogen, aryl, alkyl, arylalkyl or heteroaryl;

$R^9$ is hydrogen, alkyl, aryl, R$^{10}$-substituted aryl, heteroaryl or arylalkyl;

$R^{10}$ is selected from the group consisting of aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ may be the same or different and are independently selected from the group consisting of hydrogen, alkyl, aryl, and aralkyl;

$R^{11}$ is hydrogen, alkyl or arylalkyl;

$R^{12}$ is —C(O)R$^{13}$, —S(O)$_2$R$^{13}$, —C(O)NR$^3$R$^4$ or —C(O)OR$^{13}$;

and $R^{13}$ is alkyl, aryl, R$^{10}$-substituted aryl, heteroaryl or arylalkyl.

In another aspect, the present application provides a compound, or pharmaceutically acceptable salts or solvates of said compound, said compound having the general structure shown in formula II:

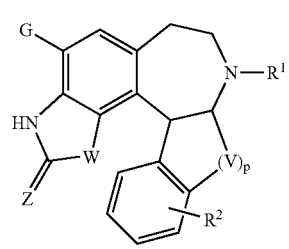

formula II wherein
p is 0, 1 or 2 and when p is 0, the carbons to which (V)$_p$ is shown connected are not linked to each other but are linked to hydrogen;

G is hydrogen, halo, alkyl, alkylthio, nitro, nitrile, hydroxy, alkoxy, alkylsulfinyl, alkylsulfonyl, trifluoromethyl or trifluromethoxy;

V is —CH$_2$—;

W is selected from the group consisting of O, S NH and N(alkyl);

Z is selected from the group consisting of NH, N(alkyl), S and O;

$R^1$ is hydrogen, alkyl, allyl, cycloalkyl or cycloalkyl (alkyl);

$R^2$ is hydrogen or 1 to 4 substituents which can be the same or different, each $R^2$ being independently selected from the group consisting of halogen, alkyl, alkylthio, alkylsulfonyl, hydroxy, alkoxy, trifluoromethyl, trifluoromethoxy, aryl, —CH=O, —NO$_2$, —NR$^{11}$R$^{12}$, CN, R$^{10}$-substituted aryl, heteroaryl, —C(O)OR$^8$, —C(O)NR$^3$R$^4$, —S(O)$_2$NR$^3$R$^4$, —C(R$^7$R$^8$)NR$^5$R$^6$, —C(R$^7$)=NOR$^4$ and —C(R$^7$R$^8$)OR$^6$;

$R^3$ is aryl, R$^{10}$-substituted aryl, arylalkyl, heteroaryl, alkyl or hydrogen;

$R^4$ is aryl, R$^{10}$-substituted aryl, heteroaryl, alkyl or hydrogen, or R$^3$, R$^4$ and N of —NR$^3$R$^4$ together can be joined together to form a ring selected from the group consisting of azetidine, R$^8$-substituted azetidine, pyrrolidine, R$^8$-substituted pyrrolidine, piperidine, R$^8$-substituted piperidine, piperazine, R$^8$-substituted piperazine, morpholine and R$^8$-substituted morpholine;

$R^5$ is alkyl, arylalkyl, —C(O)NR$^3$R$^4$, —S(O)$_2$NR$^3$R$^4$, —S(O)$_2$R$^8$, —C(O)R$^8$, —C(O)OR$^8$ or —R$^9$O-alkyl;

$R^6$ is hydrogen, alkyl, aryl, R$^{10}$-substituted aryl, heteroaryl or arylalkyl, or R$^5$, R$^6$ and N in —NR$^5$R$^6$ together can be joined together to form a ring selected from the group consisting of azetidine, R$^8$-substituted azetidine, pyrrolidine, R$^8$-substituted pyrrolidine, piperidine, $R^8$-substituted piperidine, piperazine, $R^8$-Substituted piperazine, morpholine and $R^8$-substituted morpholine;

$R^7$ is hydrogen, alkyl, aryl or arylalkyl;

$R^8$ is hydrogen, aryl, alkyl, arylalkyl or heteroaryl;

$R^9$ is hydrogen, alkyl, aryl, $R^{10}$-substituted aryl, heteroaryl or arylalkyl;

$R^{10}$ is selected from the group consisting of aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl;

$R^{11}$ is hydrogen, alkyl or arylalkyl;

$R^{12}$ is —$C(O)R^{13}$, —$S(O)_2R^{13}$, —$C(O)NR^3R^4$ or —$C(O)OR^{13}$;

and $R^{13}$ is alkyl, aryl, $R^{10}$-substituted aryl, heteroaryl or arylalkyl.

The compounds of formulae I and II can be useful as $D_1/D_5$ receptor antagonists and can be useful in the treatment of CNS disorders, metabolic disorders such as obesity and eating disorders such as hyperphagia. Another embodiment of this invention is directed to pharmaceutical compositions for the treatment of obesity which comprise an obesity treating amount of a compound of formulae I or II, or a pharmaceutically acceptable salt of said compounds, and a pharmaceutically acceptable carrier therefore.

DETAILED DESCRIPTION OF THE INVENTION

In one embodiment, the present invention provides compounds which are represented by structural formulae I and II, or a pharmaceutically acceptable salt or solvate thereof, wherein the various moieties are as described above.

In preferred embodiments of formulae I and II, G is halo, $R^1$ is hydrogen, alkyl, cyclopropyl or cyclopropylmethyl and $R^2$ is hydrogen.

In another preferred embodiments of formulae I and II, G is chloro.

In another preferred embodiments of formulae I and II, $R^1$ is hydrogen or methyl.

A preferred group of compounds are shown below in Table 1.

The compounds of formulae I and II can be administered as racemic mixtures or enantiomerically pure compounds.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least one nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 3 to about 10 carbon atoms. Preferred cycloalkyl rings contain about 3 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkylalkyl group. Non-limiting examples of suitable cycloalkylalkyl groups include cyclopropylmethyl and cyclopropylethyl. The bond to the parent moiety is through the alkyl.

"Halogen" means fluorine, chlorine, bromine, or iodine. Preferred are fluorine, chlorine or bromine, and more preferred are fluorine and chlorine.

"Halo" means fluoro, chloro, bromo, or iodo groups. Preferred are fluoro, chloro or bromo, and more preferred are fluoro and chloro.

"Ring system substituent" means a substituent attached to an aromatic or non-aromatic ring system, which, for example, replaces an available hydrogen on the ring system. Ring system substituents may be the same or different, each being independently selected from the group consisting of aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, pyrrolidonyl, tetrahydrothiophenyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Alkylsulfinyl" means an alkyl-S(O)— group. Preferred groups are those in which the alkyl group is lower alkyl. The bond to the parent moiety is through the sulfinyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in formulae I and II, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formulae I and II or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in antagonizing the dopamine receptor and thus producing the desired therapeutic, ameliorative or preventative effect.

The compounds of formulae I and II can form salts, which are also within the scope of this invention. Reference to the compounds of formulae I and II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when compounds of formulae I and II contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formulae I and II may be formed, for example, by reacting a compounds of formulae I and II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formulae I and II, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Compounds of formula I and II can have reduced potency at the Cytochrome P450 2D6 receptor and therefore can have reduced potential for affecting the metabolism of other drugs.

Compounds of formula I and II can be highly selective, high affinity $D_1/D_5$ receptor antagonists useful for the treatment of obesity.

Another aspect of this invention is a method of treating a patient (e.g., human) having a disease or condition therapeutically treated by administering a therapeutically effective amount of at least one compound of formula I or II, or a pharmaceutically acceptable salt or solvate, of said compound to the patient.

A useful dosage is about 0.001 to 100 mg/kg of body weight/day of the compound of formula I or II. A preferred dosage is about 0.01 to 25 mg/kg of body weight/day of a compound of formula I or II, or a pharmaceutically acceptable salt or solvate of said compound.

Another aspect of this invention is directed to a method of treating obesity comprising administering to a patient in need of such treatment a therapeutically effective amount of at least one compound of formula I or II, or a pharmaceutically acceptable salt or solvate of said compound.

Another aspect of this invention is directed to a method for treating eating and metabolic disorders such as bulimia or anorexia comprising administering to a patient a therapeutically effective amount of at least one compound of formula I or II, or a pharmaceutically acceptable salt or solvate of said compound.

Another aspect of this invention is directed to a method for treating hyperlipidemia comprising administering to a patient a therapeutically effective amount of at least one compound of formula I or II, or a pharmaceutically acceptable salt or solvate of said compound.

Another aspect of this invention is directed to a method for treating cellulite and fat accumulation comprising administering to a patient a therapeutically effective amount of at least one compound of formula I or II, or a pharmaceutically acceptable salt or solvate of said compound.

Another aspect of this invention is directed to a method for treating type II diabetes comprising administering to a patient a therapeutically effective amount of at least one compound of formula I or II, or a pharmaceutically acceptable salt or solvate of said compound.

In addition to the "direct" effect of the compounds of this invention on the $D_1/D_5$ receptor, there are diseases and conditions that can benefit from weight loss such as insulin resistance, impaired glucose tolerance, Type II Diabetes, hypertension, hyperlipidemia, cardiovascular disease, gall stones, certain cancers, and sleep apnea.

The compounds of formulae I and II are expected to be useful in the therapy of a patient suffering from obsessive compulsive disorder, a somatoform disorder, a dissociative disorder, an eating disorder, an impulse control disorder, or autism by administering an effective amount of a compound of formula I or II or salt or solvate thereof.

More specifically the compounds of formulae I and II can be useful in the treatment of a variety of eating disorders including (but not limited to) anorexia nervosa, bulimia, and binge eating.

Compounds of formulae I and II can be useful in the treatment of a variety of impulse control disorders including (but not limited to) pathological gambling, trichotillomania, compulsive buying, and sexual compulsion.

The compounds of the invention (i.e., the compounds of formula I and II) may also be used in combinations with other compounds as described below. Accordingly, another aspect of this invention is a method for treating obesity comprising administering to a patient (e.g., a female or male human)

a. an amount of a first compound, said first compound being a compound of the invention, a solvate thereof, or a pharmaceutically acceptable salt of said compound or of said solvate; and
b. an amount of a second compound, said second compound being an anti-obesity and/or anorectic agent such as a $\beta_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a. a first compound, said first compound being a compound of the invention, a solvate thereof, or a pharmaceutically acceptable salt of said compound or of said solvate; and
b. a second compound, said second compound being an anti-obesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:

a. an amount of a compound of the invention, a solvate thereof, or a pharmaceutically acceptable salt of said compound or of said solvate and a pharmaceutically acceptable carrier, vehicle or diluent in a first unit dosage form;
b. an amount of an anti-obesity and/or anorectic agent such as a $\beta_3$ agonist, a thyromimetic agent, an anoretic agent, or an NPY antagonist and a pharmaceutically acceptable carrier, vehicle or diluent in a second unit dosage form; and
c. means for containing said first and second dosage forms wherein the amounts of the first and second compounds result in a therapeutic effect.

Preferred anti-obesity and/or anorectic agents (taken singly or in any combination thereof) in the above combination methods, combination compositions and combination kits include: phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a Gl lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a patient (e.g., a female or male human)

a. an amount of a first compound, said first compound being a compound of the invention, a solvate thereof, or a pharmaceutically acceptable salt of said compound or of said solvate; and
b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of the invention, a solvate thereof, or a pharmaceutically acceptable salt of said compound or of said solvate; a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:
a. an amount of a compound of the invention, a solvate thereof, or a pharmaceutically acceptable salt of said compound or of said solvate and a pharmaceutically acceptable carrier, vehicle or diluent in a first unit dosage form;
b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and
c. means for containing said first and second dosage forms wherein the amounts of the first and second compounds result in a therapeutic effect.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any methods known to the art for the manufacture of pharmaceutical compositions. Such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients include without limitation, inert diluents, such as calcium carbonate, sodium carbonate, lactose, calcium phosphate or sodium phosphate; granulating and disintegrating agents such as corn starch, or alginic acid; binding agents such as starch, gelatin, or acacia, and lubricating agents such as magnesium stearate, stearic acid or talc. The tablets may be uncoated or they may be coated by known techniques to delay disintegration and absorption in the gastrointestinal tract, and thereby provide a sustained action over a longer period. For example, a time delay material such as glyceryl monostearate or glyceryl diasterate may be employed. They may also be coated by the technique described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin; or as soft gelatin capsules wherein the active ingredient is mixed with water or an oil medium such as peanut oil, liquid paraffin or olive oil.

Aqueous suspensions contain the active material in admixture with excipients suitable for the manufacture of such suspensions. Such excipients are suspending agents such as sodium carboxymethylcellulose, methylcellulose, hydroxypropylmethylcellulose, sodium alginate, polyvinyl pyrrolidone, gum tragacanth and gum acacia. Dispersing or wetting agents may be a naturally occurring phosphatide such as lecithin, or condensation products of an alkylene oxide with fatty acids, for example, polyoxyethylene stearate, or condensation products of ethylene oxide with long chain aliphatic alcohols such as heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate. The aqueous suspensions may also contain one or more preservatives, for example, ethyl or n-propyl p-hydroxybenzoate; one or more coloring agents, one or more flavoring agents, and one or more sweetening agents such as sucrose, saccharin, aspartame or the like.

Oily suspensions may be formulated by suspending the active ingredient in a vegetable oil such as arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those mentioned above. Additional excipients such as sweetening, flavoring and coloring agents may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents, which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formulae I and II or their pharmaceutical compositions may also be administered in the form of suppositories for rectal administration of the drug. These compositions can be prepared by mixing the drug with a suitable non-irritating excipient, which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of formulae I and II or their pharmaceutical compositions are employed. (For purposes of this application, topical application shall include mouth washes and gargles.)

The compounds of formulae I and II or their pharmaceutical compositions can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds or the pharmaceutical compositions of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of formulae I and II or their pharmaceutical compositions of the present invention, is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compounds of structural formulae I and II useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.01 mg/kg to 500 mg/kg of bodyweight. The range is more particularly from about 0.01 mg/kg to 150 mg/kg of body weight per day or most particularly 0.01 mg/kg to 10 mg/kg.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

A preferred group of compounds are those listed below in Table 1.

TABLE 1

| Compound | Structure | $D_1$ ($K_i$, nM) | $D_2$ ($K_i$, nM) |
|---|---|---|---|
| 8 | 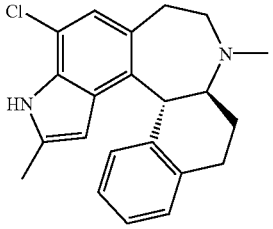 | 24.7 | 232 |
| 15A | 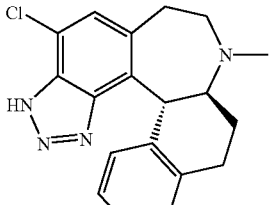 | 146 | 1529 |
| 13A | 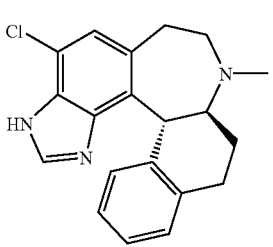 | 248 | 984 |
| 16A | 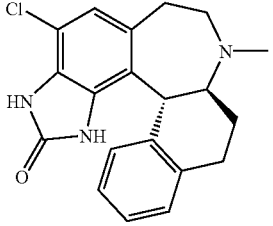 | 7 | 1023 |

TABLE 1-continued

| Compound | Structure | D₁ (Kᵢ, nM) | D₂ (Kᵢ, nM) |
|---|---|---|---|
| 18A | 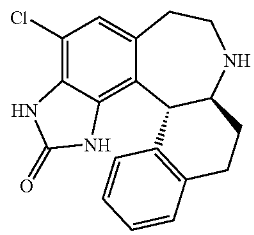 | 16.5 | 3271 |
| 17A | 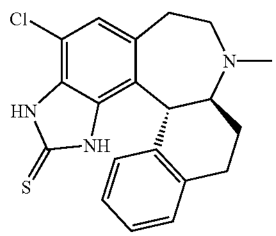 | 40 | 1044 |
| 25A | 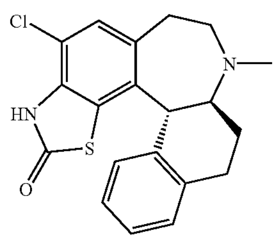 | 2.1 | 257 |
| 26A | 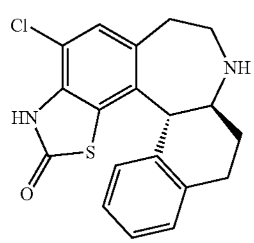 | 6.5 | 661 |
| 4 | 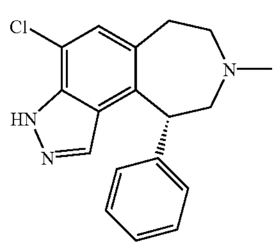 | 14 | 3551 |
| 6 | 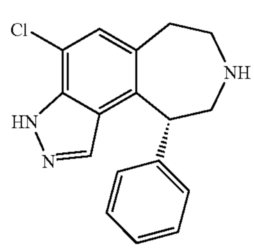 | 183 | 5012 |
| 16B | | 350 | 10000 |
| 18B | | 1898 | 10000 |
| 17B | | 1787 | 10000 |
| 25B | | 115 | 2891 |
| 26B | | 1082 | 3196 |
| 27 | | 1.9 | 336 |

TABLE 1-continued
| Compound | Structure | D₁ (K$_i$, nM) | D₂ (K$_i$, nM) |
|---|---|---|---|
| 18C | 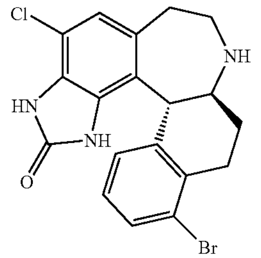 | 11.3 | 648 |
| 16C | 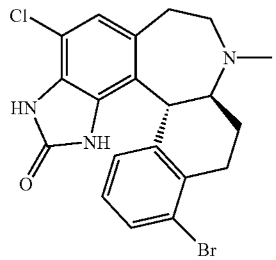 | 6.1 | 172 |
Compounds such as 1, 2, 3, 4 and 5 can be prepared by procedures A, B, C and D as show below (Scheme 1) from a compound of formula III
formula III
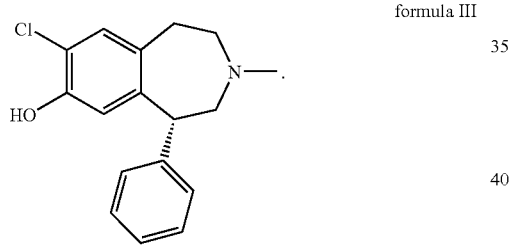
Scheme 1
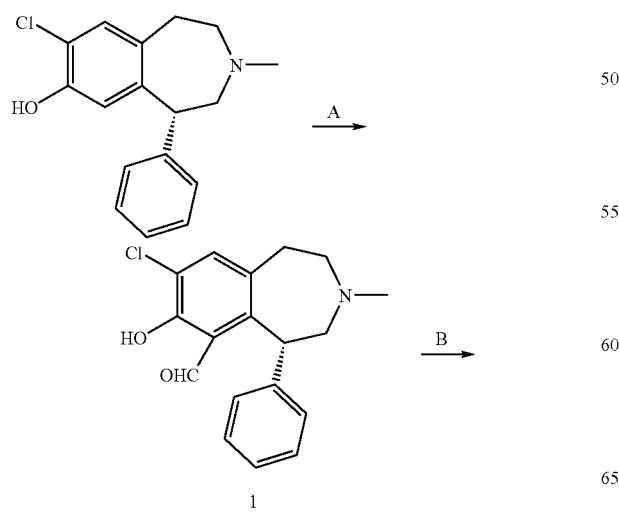
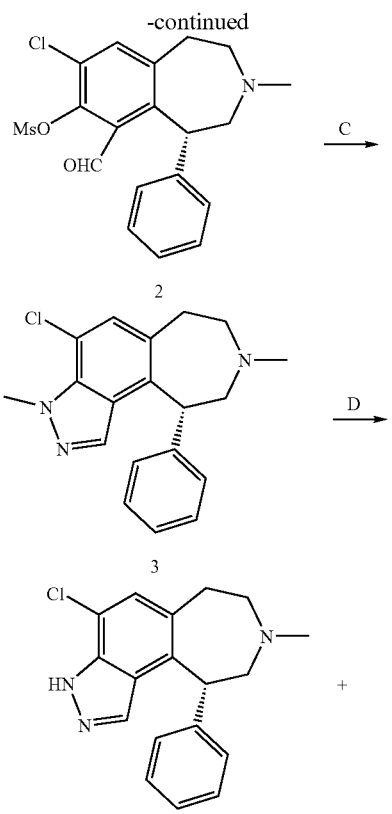
Compounds represented by the formulae 6, 7 and 8 can be prepared from Procedures E, F and G as show below (Scheme 2).
Scheme 2
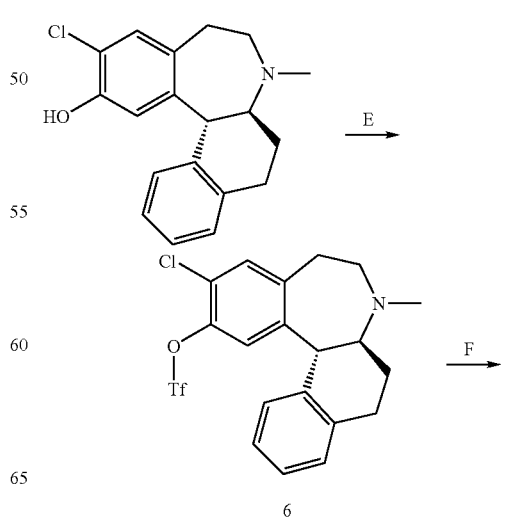

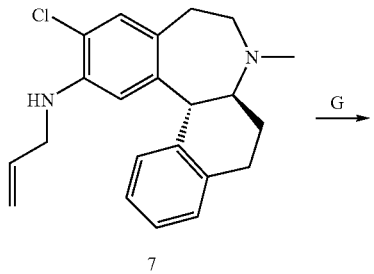
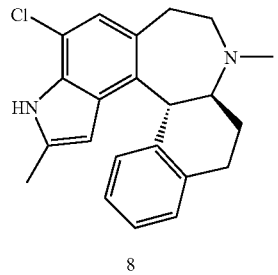
Compounds represented by formulae 9A, 10A, 11A, 12A, 13A, 14A, 15A, 16A, 17A and 18A can be prepared by procedures H, I, J, K, L, M, N, O, P and Q according to Scheme 3, described below.
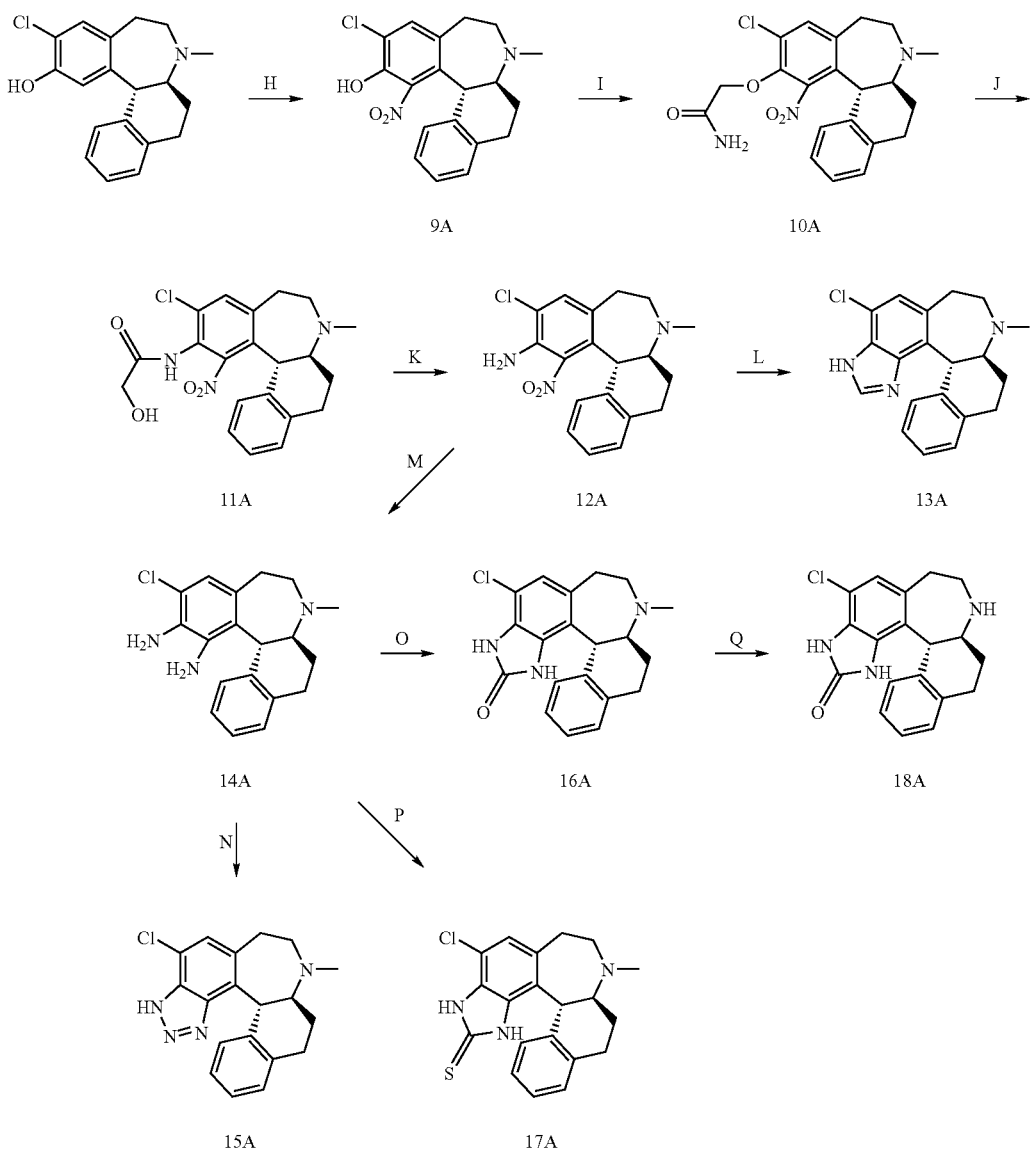

Compounds of formulae 9B, 10B, 11B, 12B, 14B, 16B, 17B, and 18B can be synthesized by procedures H, I, J, K, M, O, P and Q as described below in scheme 4.
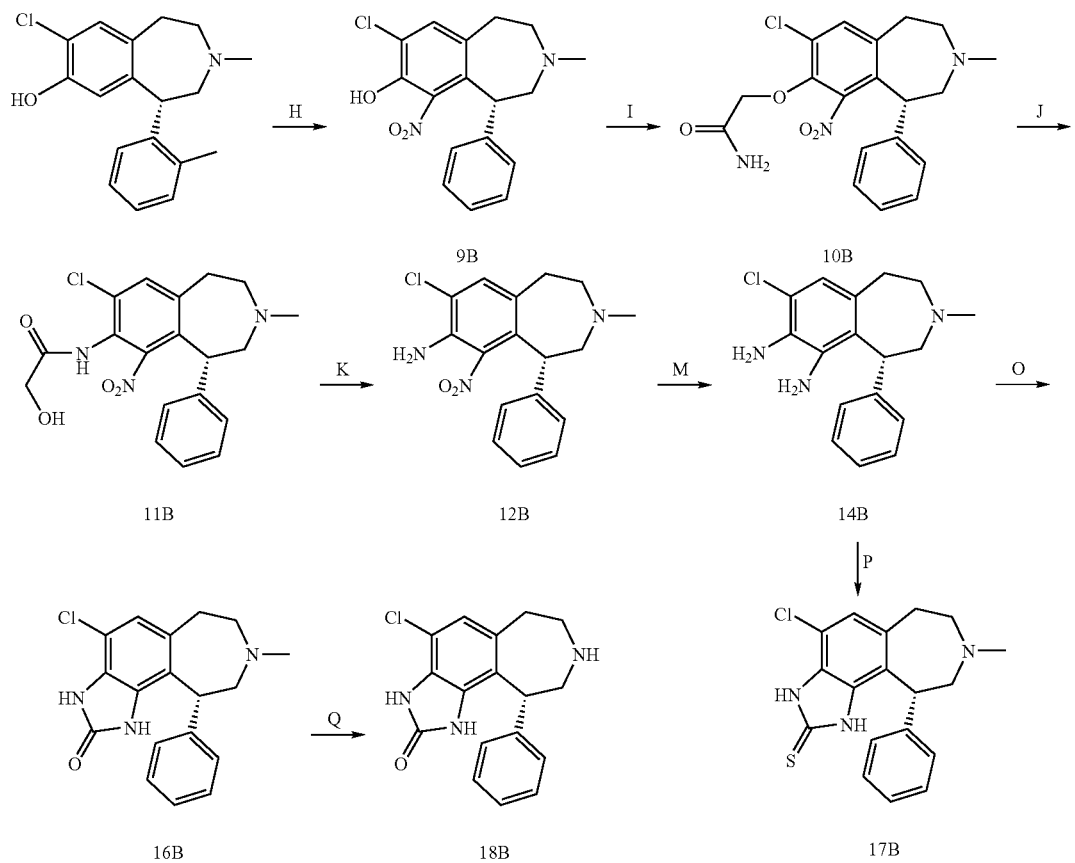
Scheme 4
The synthetic route to compounds such as 19A, 20A, 21A, 22A, 23A, 24A, 25A and 26A is described in scheme 5 using procedures R, S, T, U, V, W, X and Y.
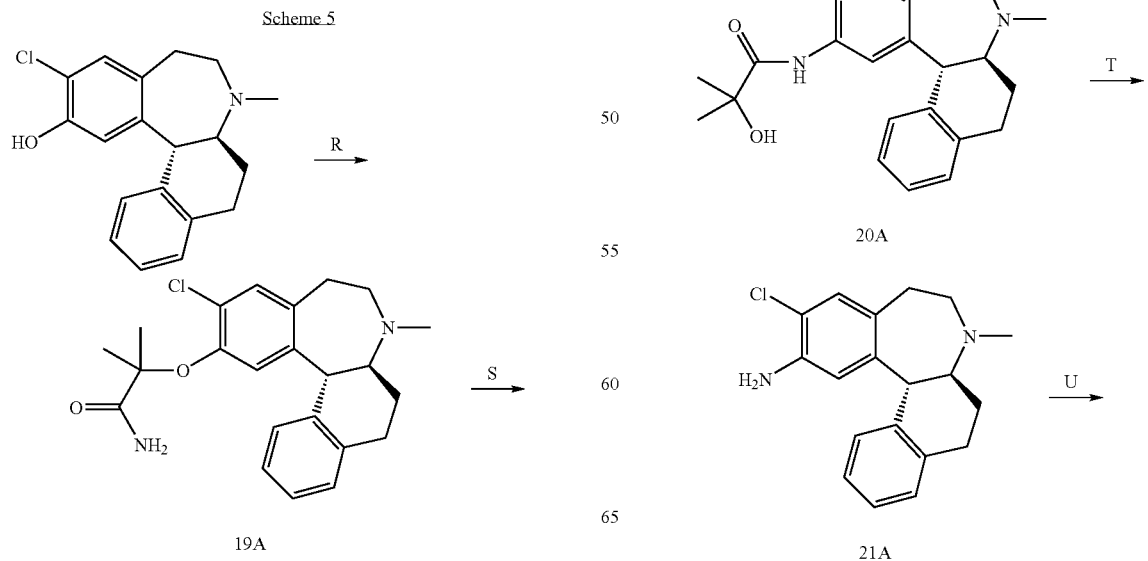
Scheme 5

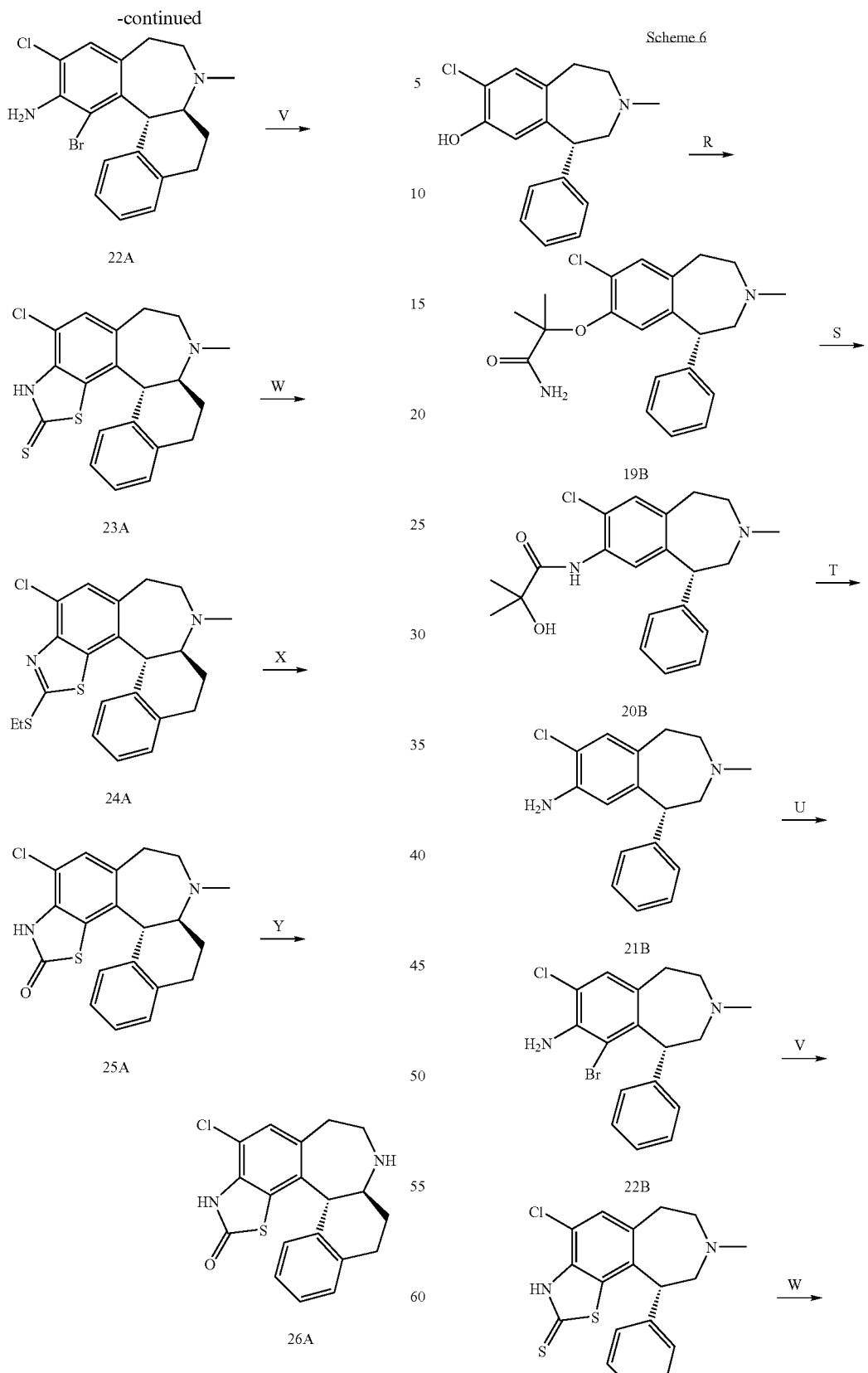
The synthetic route to compounds such as 19B, 20B, 21B, 22B, 23B, 24B, 25B and 26B is described in scheme 6 using procedures R, S, T, U, V, W, X and Y.

-continued
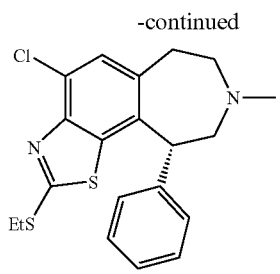
24B
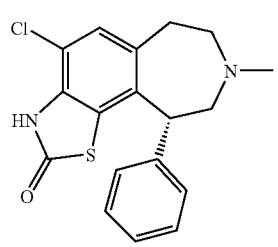
25B
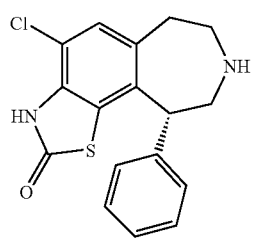
26B
-continued
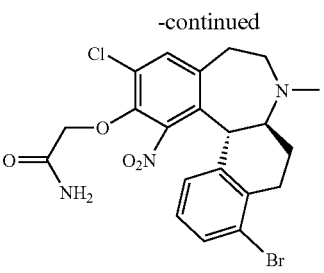
10C
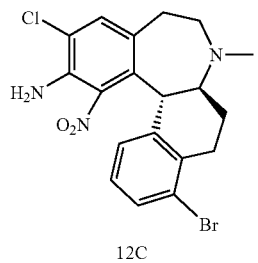
12C
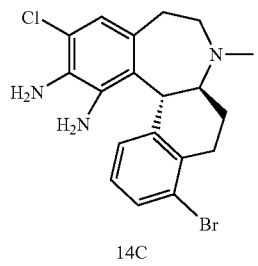
14C
The synthetic route to compounds such as 9C, 10C, 12C, 14C, 16C, 18C and 27 is described in scheme 7 using procedures H, I, J, K, L O, Q and Z.
Scheme 7
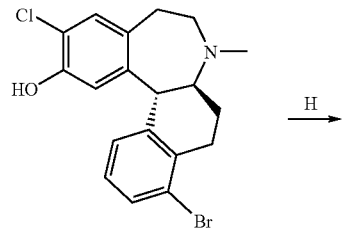
10-Br-
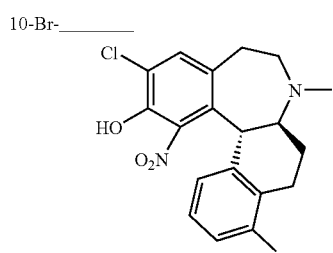
9C
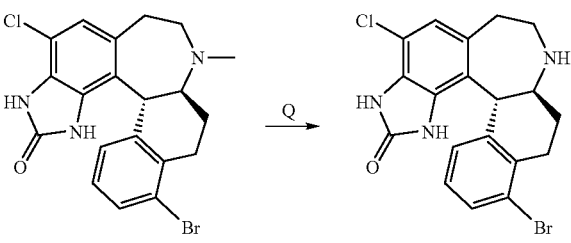
16C        18C
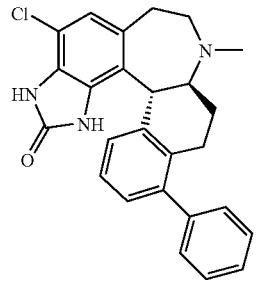
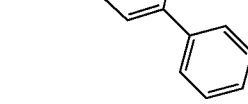
27

The following solvents and reagents may be referred to by their abbreviations:
Di-tert-butyl dicarbonate: (Boc)$_2$O
boron trifluoride diethyl etherate: BF$_3$.OEt$_2$
2,2'-Bis(diphenylphosphino)-1,1'-binaphthyl: BINAP
t-butyloxycarbonyl: -Boc
ethyl acetate: AcOEt or EtOAc
Thin layer chromatography: TLC
preparative thin layer chromatography: PTLC
4-dimethylaminopyridine: DMAP
milliliters: mL
millimoles: mmol
milligrams: mg
grams: g
hours: h
minutes: min
centigrade: C°
room temperature (ambient) about 25° C. (rt).

Experimental Procedures

Procedure A:

A mixture of 2.88 g (10 mmol) of a compound of formula III, 1.4 g (10 mmol) of hexamethylenetetramine in 60 mL of TFA was heated under reflux for 42 h. The solvent was evaporated; the residue was quenched with 200 mL of saturated NaHCO$_3$. It was extracted with three portions of 150 mL of EtOac. The combined organic extracts were washed with brine (80 mL) and concentrated. The residue was chromatographed on silica gel eluting with 0.5 to 3% MeOH in CH$_2$Cl$_2$ to give 1.02 g of compound 1. Calcd m/z for C$_{18}$H$_{18}$ClNO$_2$.H$^+$=316.1. found m/z=316.1.

Procedure B:

To a stirred solution of 1.0 g (3.2 mmol) of compound 1, 0.63 g (6.3 mmol) of triethylamine (Et$_3$N) and 0.01 g of DMAP in 20 mL of CH$_2$Cl$_2$ was added 0.44 g (3.8 mmol) of methanesulfonyl chloride at 0° C. The mixture was warmed to room temperature and stirred for 18 h. It was diluted with 200 mL of ethyl acetate, washed with 80 mL of saturated NaHCO$_3$ and 50 mL of brine. The organic layer was concentrated to give 1.26 g of crude product 2. Calcd m/z for C$_{19}$H$_{20}$ClNO$_4$S.H$^+$=394.1. found m/z=394.1.

Procedure C:

A mixture of 0.8 g (2 mmol) of compound 2, 0.19 g (4 mmol) of methylhydrazine and 0.39 g (5 mmol) of ammonium acetate in 60 mL of m-xylene was stirred at 135° C. for 15 min, then stirred at 150° C. for 3 days with azeotropic removal of water using a Dean-Starker apparatus. The solvent was evaporated; the residue was diluted with 150 mL of saturated NaHCO$_3$. It was extracted with three portions of 100 mL of ethyl acetate. The combined organic extracts were washed with 80 mL of brine and concentrated. The residue was chromatographed on silica gel eluting with 1 to 2% MeOH in CH$_2$Cl$_2$ to give 0.53 g of compound 3. Calcd m/z for C$_{19}$H$_{20}$ClN$_3$.H$^+$=326.1. found m/z=326.1.

Procedure D:

A mixture of 8.5 g of pyridine and 10 mL of concentrated HCl was distilled at 225° C. To this solution was added 0.33 g (1 mmol) of compound 3. The mixture was stirred at 225° C. for 2 h, then cooled to room temperature. The solid was dissolved in dilute NH$_4$OH. The aqueous solution was extracted with three portions of 100 mL of ethyl acetate. The combined organic extracts were washed with 50 mL of brine and concentrated. The residue was purified by preparative TLC eluting with 10% MeOH in CH$_2$Cl$_2$ to give 0.083 g of compound 4 and 0.067 g of 5. Compound 4: Calcd m/z for C$_{18}$H$_{18}$ClN$_3$.H$^+$=312.1. found m/z=312.1. Compound 5: Calcd m/z for C$_{17}$H$_{16}$ClN$_3$.H$^+$=298.1; found m/z=298.1

Procedure E:

To a stirred suspension of 2.2 g (7 mmol) of ecopipam in 40 mL of CH$_2$Cl$_2$ was added 2.1 g (20 mmol) of Et$_3$N and 3 g (10.5 mmol) of triflic anhydride at −20° C. The mixture was warmed to room temperature with stirring over a period of 3 h. It was quenched with 60 mL of saturated NaHCO$_3$, extracted with two portions of 60 mL of ethyl acetate. The combined organic extracts were washed with 30 mL of brine, concentrated. The residue was chromatographed on silica gel eluting with 1 to 2% MeOH in CH$_2$Cl$_2$ to give 1.86 g of compound 6. Calcd m/z for C$_{20}$H$_{19}$ClF$_3$NO$_3$S.H$^+$=446.1. found m/z=446.1

Procedure F:

A mixture of 0.89 g (2 mmol) of compound 6, 0.04 g (0.18 mmol) of Pd(OAc)$_2$, 0.17 g (0.27 mmol) of BINAP, 0.22 g (3.8 mmol) of allyl amine and 0.91 g of Cs$_2$CO$_3$ in 5 mL of toluene was stirred at room temperature for 30 min. The reaction was stirred at 100° C. for 10 h, then cooled to room temperature and filtered. The filtrate was concentrated. The residue was purified by preparative TLC eluting with 10% MeOH in CH$_2$Cl$_2$ to give 0.09 g of compound 7. Calcd m/z for C$_{22}$H$_{25}$ClN$_2$.H$^+$=353.18. found m/z=353.1.

Procedure G:

A mixture of 0.05 g (0.14 mmol) of compound 7A, 0.1 mL of BF$_3$.OEt$_2$ in 2 mL of sulfolane was stirred at 215° C. for 6 h. It was cooled to room temperature, quenched with 25 mL of saturated NaHCO$_3$. The aqueous solution was extracted with two portions of 20 mL of ethyl acetate. The combined organic extracts were washed with 10 mL of brine and concentrated. The residue was purified by preparative TLC eluting with 10% MeOH in CH$_2$Cl$_2$ to give 0.01 g of compound 8. Calcd m/z for C$_{22}$H$_{23}$ClN$_2$.H$^+$=351.16; found m/z=351.16.

Procedure H:

To a stirred solution of 3.14 g (10 mmol) of ecopipam in 25 mL of formic acid was added 1.3 mL (19.5 mmol) of concentrate nitric acid at 0° C. The mixture was warmed to room temperature over a period of 3 h and stirred for 18 h. The solvent was evaporated, the residue was slowly added to 300 mL of saturated NaHCO$_3$; the yellow precipitate was collected by filtration to give compound 9A. Calcd m/z for C$_{19}$H$_{19}$ClN$_2$O$_3$.H$^+$=359.1; found m/z=359.1.

Compound 9B and 9C can be prepared analogously. 9B: Calcd m/z for C$_{17}$H$_{17}$ClN$_2$O$_3$.H$^+$=333.1; found m/z=333.1. 9C: Calcd m/z for C$_{19}$H$_{18}$BrClN$_2$O$_3$.H$^+$=437.03; found m/z=437.1

Procedure I:

A mixture of 5.38 g (15 mmol) of compound 9A, 2.28 g (16.5 mmol) of bromoacetamide and 5 g (36 mmol) of K$_2$CO$_3$ in 150 mL of acetone was heated under reflux for 70 h. The solvent was evaporated. The residue was diluted with 150 mL of H$_2$O, and extracted with four portions of 150 mL of ethyl acetate. The combined organic extracts were washed with 100 mL of brine and concentrated. The residue was chromatographed on silica gel eluting with 1 to 4% MeOH in CH$_2$Cl$_2$ to give 5.66 g of compound 10A. Calcd m/z for C$_{21}$H$_{22}$ClN$_3$O$_4$.H$^+$=416.1; found m/z=416.1.

Compound 10B and 10C can be prepared analogously. 10B: Calcd m/z for C$_{19}$H$_{20}$ClN$_3$O$_4$.H$^+$=390.1; found m/z=390.1. 10C: Calcd m/z for C$_{21}$H$_{21}$BrClN$_3$O$_4$.H$^+$=494.05; found m/z=494.1.

Procedure J:

A mixture of 0.42 g (1 mmol) of compound 10A, 0.2 g (5 mmol) of NaOH in 5 mL of DMF was stirred at room temperature under nitrogen atmosphere for 2 h. It was quenched with 50 mL of saturated $NaHCO_3$, and extracted with three portions of 50 mL of ethyl acetate. The combined organic extracts were washed with 30 mL of brine and concentrated to give 0.41 g of compound 11A. Calcd m/z for $C_{21}H_{22}ClN_3O_4.H^+=416.1$; found m/z=416.1.

Compound 11B can be prepared analogously. 11B: Calcd m/z for $C_{19}H_{20}ClN_3O_4.H^+=390.1$; found m/z=390.1.

Procedure K:

A solution of 0.41 g (1 mmol) of compound 11A in 3 mL of concentrated HCl and 3 mL of 1,4-dioxane was heated under reflux for 2 h. After cooling, it was quenched with 50 mL of saturated $NaHCO_3$ and extracted with two portions of 50 mL of ethyl acetate. The combined organic extracts were washed with 30 mL of brine and concentrated. The residue was chromatographed on silica gel eluting with 1 to 3% MeOH in $CH_2Cl_2$ to give 0.32 g of compound 12A. Calcd m/z for $C_{19}H_{20}ClN_3O_2.H^+=358.1$; found m/z=358.1.

Compound 12B and 12C can be prepared analogously. 12B: Calcd m/z for $C_{17}H_{18}ClN_3O_2.H^+=332.1$; found m/z=332.1. 12C: Calcd m/z for $C_{19}H_{19}BrClN_3O_2.H^+=436.04$; found m/z=436.1.

Procedure L:

To a mixture of 0.18 g (0.5 mmol) of compound 12A, 0.5 g of iron power in 2 mL of HCOOH and 2 mL of $H_2O$ was added 2 mL of concentrate HCl. The mixture was refluxed for 2 h. After cooling to room temperature, it was quenched with 80 mL of saturated $NaHCO_3$ and extracted with 60 mL of ethyl acetate three times. The combined organic extracts were washed with 30 mL of brine, concentrated. The residue was chromatographed on silica gel eluting with 1 to 3% MeOH in $CH_2Cl_2$ to give 0.16 g of compound 13A. Calcd m/z for $C_{20}H_{20}ClN_3.H^+=338.1$; found m/z=338.1.

Procedure M:

To a mixture of 0.6 g (1.68 mmol) of compound 12A and 1 g of iron power in 10 mL of $H_2O$ was added 10 mL of concentrate HCl. The mixture was heated under reflux for 1 h. After cooling to room temperature, it was quenched with saturated $NaHCO_3$ and extracted with three portions of 100 mL of ethyl acetate. The combined organic extracts were washed with 30 mL of brine and concentrated to give 0.56 g of compound 14A. Calcd m/z for $C_{19}H_{22}ClN_3.H^+=328.1$; found m/z=328.1.

Compound 14B and 14C can be prepared analogously. 14B: Calcd m/z for $C_{17}H_{20}ClN_3.H^+=302.1$; found m/z=302.1. 14C: Calcd m/z for $C_{19}H_{21}BrClN_3.H^+=406.07$; found m/z=406.1.

Procedure N:

To a stirred solution of 0.055 g (0.17 mmol) of compound 14A in 2 mL of concentrated HCl was slowly added a solution of 0.014 g (0.2 mmol) of $NaNO_2$ in 1.2 mL of $H_2O$ at room temperature. After stirring for 3 h, it was quenched with 30 mL of saturated $NaHCO_3$ and extracted with two portions of 40 mL of ethyl acetate. The combined organic extracts were washed with 20 mL of brine and concentrated. The residue was purified by preparative TLC eluting with 10% MeOH in $CH_2Cl_2$ to give 0.048 g of compound 15A. Calcd m/z for $C_{19}H_{19}ClN_4.H^+=339.1$; found m/z=339.1.

Procedure O:

To a solution of 0.064 g (0.2 mmol) of compound 14A and 0.025 g (0.2 mmol) of DMAP in 2 mL of acetonitrile ($CH_3CN$) was added a solution of 0.048 g (0.22 mmol) of $(Boc)_2O$ in 1 mL of acetonitrile. The mixture was stirred at room temperature for 1 h, then concentrated. The residue was purified by preparative TLC eluting with 10% MeOH in $CH_2Cl_2$ to give 0.048 g of compound 16A. Calcd m/z for $C_{20}H_{20}ClN_3O.H^+=354.1$; found m/z=354.1.

Compound 16B and 16C can be prepared analogously. 16B: Calcd m/z for $C_{18}H_{18}ClN_3O.H^+=328.1$; found m/z=328.1. 16C: Calcd m/z for $C_{20}H_{19}BrClN_3=432.05$; found m/z=432.1.

Procedure P:

To a solution of 0.05 g (0.15 mmol) of compound 14A and 0.02 g (0.16 mmol) of DMAP in 3 mL of acetonitrile was added a solution of 0.081 g (0.46 mmol) of thiocarbonyldiimidazole in 2 mL of acetonitrile. The mixture was stirred at room temperature for 5 h, then concentrated. The residue was purified by preparative TLC eluting with 10% MeOH in $CH_2Cl_2$ to give 0.04 g of compound 17A. Calcd m/z for $C_{20}H_{20}ClN_3S.H^+=370.1$; found m/z=370.1.

Compound 17B can be prepared analogously. 17B: Calcd m/z for $C_{18}H_{18}ClN_2S.H^+=344.1$; found m/z=344.1.

Procedure Q:

A mixture of 8.5 g of pyridine and 10 mL of concentrated HCl was distilled at 225° C. To this solution was added 0.14 g (0.39 mmol) of compound 16A-HCl salt. The mixture was stirred at 225° C. for 6 h, cooled to room temperature. The solid was dissolved in dilute $NH_4OH$. The aqueous solution was extracted with three portions of 100 mL of ethyl acetate. The combined organic extracts were washed with 80 mL of brine and concentrated. The residue was purified by preparative TLC eluting with 10% MeOH in $CH_2Cl_2$ to give 0.082 g of compound 18A. Calcd m/z for $C_{19}H_{18}ClN_3O.H^+=340.1$; found m/z=340.1.

Compound 18B and 18C can be prepared analogously. 18B: Calcd m/z for $C_{17}H_{16}ClN_3O.H^+=314.1$; found m/z=314.1. 18C: Calcd m/z for $C_{19}H_{17}BrClN_3O.H^+=418.03$; found m/z=418.1.

Procedure R:

To a stirred solution of 3.14 g (10 mmol) of ecopipam in 50 mL of dioxane was added 0.6 g (60%, 15 mmol) of sodium hydride. After stirring at room temperature for 1 h, 2-bromo-2-methylpropanamide (1.66 g, 10 mmol) was slowly introduced at 0° C. The resulting reaction was stirred at reflux overnight. It was cooled, partitioned between 50 mL of $CH_2Cl_2$ and 50 mL of $H_2O$. The aqueous layer was extracted with four portions of 25 mL of $CH_2Cl_2$. The combined organic extracts were washed with 100 mL of brine, and concentrated to give a mixture of desired compound 19A and ecopipam with a ratio of 60:40. Calcd m/z for $C_{23}H_{27}ClN_2O_2.H^+=399.18$; found m/z=399.1.

Compound 19B can be prepared analogously. 19B: Calcd m/z for $C_{21}H_{25}ClN_2O_2.H^+=373.17$; found m/z=373.1.

Procedure S:

To a stirred solution of 3.58 g of the above mixture of compound 19A and ecopipam in 60 mL of DMF was added 1.08 g (60%, 27 mmol) of sodium hydride at 0° C. The mixture was stirred at 50° C. overnight. It was cooled to room temperature, partitioned between 100 mL of water and 100 mL of ether. The aqueous layer was extracted with 50 mL of ether and five portions of 50 mL of ethyl acetate. The combined organic extracts were washed with brine and concentrated. The residue was chromatographed over silica gel eluting with 2 to 3% MeOH in $CH_2Cl_2$ to give 1.91 g of compound 20A. Calcd m/z for $C_{23}H_{27}ClN_2O_2.H^+=399.18$; found m/z=399.1.

Compound 20B can be prepared analogously. 20B: Calcd m/z for $C_{21}H_{25}ClN_2O_2.H^+$=373.17; found m/z=373.1.

Procedure T:

To a stirred solution of 2.07 g (5.2 mmol) of compound 20A in 25 mL of dioxane was added 25 mL of 6N HCl. The solution was heated under reflux overnight. It was cooled to room temperature, basified with saturated $NaHCO_3$, and extracted with four portions of ethyl acetate. The combined organic extracts were washed with 50 mL of brine, then concentrated. The residue was chromatographed over silica gel eluting with 10% MeOH in $CH_2Cl_2$ to yield 1.66 g of compound 21A. Calcd m/z for $C_{19}H_{21}ClN_2.H^+$=313.15; found m/z=313.1.

Compound 21B can be prepared analogously. 21B: Calcd m/z for $C_{17}H_{19}ClN_2.H^+$=287.1; found m/z=287.1.

Procedure U:

To a stirred solution of compound 20A in 40 mL of HCOOH was added 13 mL of 1M $Br_2$ in HCOOH dropwise at 0° C. The mixture was stirred at 0–5° C. for 1.5 h, then concentrated. The residue was diluted with 100 mL of saturated $NaHCO_3$, extracted with four portions of 120 mL of ethyl acetate. The combined organic extracts were washed brine and concentrated. The residue was chromatographed eluting with 1 to 2% MeOH in $CH_2Cl_2$ to give 3.23 g of compound 22A. Calcd m/z for $C_{19}H_{20}BrClN_2.H^+$=391.1; found m/z=391.1.

Compound 22B can be prepared analogously. 22B: Calcd m/z for $C_{17}H_{18}BrClN_2.H^+$=365.04; found m/z=365.1.

Procedure V:

A mixture of 0.098 g (0.25 mmol) of compound 22A and 0.08 g (0.5 mmol) potassium eethylxanthate in 2 mL of DMF was heated at 160° C. for 16 h. It was cooled, quenched with 60 mL of saturated $NaHCO_3$, and extracted with three portions of 50 mL of ethyl acetate. The combined organic extracts were washed brine and concentrated to give crude compound 23A. Calcd m/z for $C_{20}H_{19}ClN_2S_2.H^+$=387.1; found m/z=387.1.

Compound 23B can be prepared analogously. 23B: Calcd m/z for $C_{18}H_{17}ClN_2S_2.H^+$=361.1; found m/z=361.1.

Procedure W:

A mixture of 0.079 g (0.2 mmol) of compound 23A, 0.05 g (0.3 mmol) of diethyl chlorophosphate and 0.07 g (0.5 mmol) of $K_2CO_3$ in acetone was heated under reflux for 15 h. It was concentrated, the residue was diluted with 30 mL of water and extracted with four portions of 40 mL of ethyl acetate. The combined organic extracts were washed with brine and concentrated. The residue was purified by preparative TLC eluting with 8% MeOH in $CH_2Cl_2$ plus 1% $NH_4OH$ to give 0.074 g of compound 24A. Calcd m/z for $C_{22}H_{23}ClN_2S_2.H^+$=415.1; found m/z=415.1.

Compound 24B can be prepared analogously. 24B: Calcd m/z for $C_{20}H_{21}ClN_2S_2.H^+$=389.1; found m/z=389.1.

Procedure X:

A mixture of 0.017 g (0.04 mmol) of compound 24A and 0.02 g (0.4 mmol) of sodium methoxide in 1 mL of DMF was stirred at room temperature for 64 h. It was quenched with 25 mL of water, extracted with three portions of 25 mL of ethyl acetate. The combined organic extracts were washed with brine and concentrated. The residue was purified by preparative TLC eluting with 8% MeOH in $CH_2Cl_2$ plus 1% $NH_4OH$ to give 0.010 g of compound 25A. Calcd m/z for $C_{20}H_{19}ClN_2OS.H^+$=371.1; found m/z=371.1.

Compound 25B can be prepared analogously. 25B: Calcd m/z for $C_{18}H_{17}ClN_2OS.H^+$=345.1; found m/z=345.1.

Procedure Y:

A mixture of 0.037 g (0.1 mmol) of compound 25A and 3 g of pyridine-HCl salt was heated at 225° C. for 16 h. It was cooled to room temperature, quenched with 30 mL of $H_2O$ and basified with NaOH. The aqueous solution was extracted with three portions of 30 mL of ethyl acetate. The combined organic extracts were washed brine and concentrated. The residue was purified by preparative TLC eluting with 10% MeOH in $CH_2Cl_2$ to give 0.017 g of compound 26A. Calcd m/z for $C_{19}H_{17}ClN_2OS.H^+$=357.1; found m/z=357.1.

Compound 26B can be prepared analogously. 26B: Calcd m/z for $C_{17}H_{15}ClN_2OS.H^+$=331.1; found m/z=331.1.

Procedure Z:

To a mixture of compound 16C (0.115 mmol) and 0.02 g of phenyl boronic acid (0.164 mol) in 2 mL of methanol/toluene (1:1) was added 0.5 mL of aqueous sodium carbonate solution and 0.001 g of tetrakistriphenylphosphene. The reaction mixture was heated at 90° C. for 4 h. The contents were passed through a short pad of celite and washed with ethyl acetate. The solvent was removed in vaccuo and the product was isolated by prep TLC using 5% methanol in dichloromethane as eluent to give 0.03 g of compound 27. Calcd m/z for $C_{26}H_{24}ClN_3O.H^+$=430.17; found m/z=430.1.

The compounds of the present invention exhibit $D_1/D_5$ receptor antagonizing activity, which has been correlated with pharmaceutical activity for treating CNS disorders such as OCD, trichotillomania, metabolic disorders such as obesity, eating disorders such as hyperphagia, and diabetes. This utility is manifested by activity in the following assay.

Assay

Affinity values (Ki) of compounds at human $D_1$ and $D_2$ receptors were ascertained using radioligand binding competition assays. Ltk- cells expressing $D_1$ and $D_2$ (long variant) receptors were lysed in hypotonic buffer for membrane preparation. Membranes were incubated with various concentrations of test compound and 1 nM [3H] of a compound of formula III and 0.2 nM [3H] Methylspiperone for $D_1$ and $D_2$ assays, respectively. Non-specific binding was defined as binding in the presence of 10 micromolar of a compound of formula III for $D_1$ assays and 10 micromolar butaclamol for $D_1$ assays. Following incubation to equilibrium (1 hour at room temperature), bound radioligand was separated from free by rapid filtration. Bound radioactivity on the dried filters was quantified by liquid scintillation counting.

The Ki values for $D_1$ and $D_2$ assays for the instant compounds are shown in Table 1. For the compounds of this invention, a range of $D_1$ receptor binding activity (Ki values) of from about 5 nM to about 2000 nM was observed. A range of $D_2$ receptor binding activity (Ki values) of from about 200 nM to about 10000 nM was observed. Compounds of this invention preferably have a $D_1$ binding activity in the range of from about 5 nM to about 100 nM, more preferably from about 5 to about 50 nM, and most preferably from about 5 to about 20 nM.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula

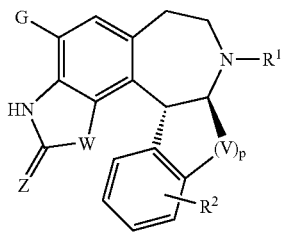

formula II or a pharmaceutically acceptable salt or solvate thereof, wherein p is 0, 1 or 2 and when p is 0, the carbons to which $(V)_p$ is shown connected are not linked to each other but are linked to hydrogen;

G is hydrogen, halo, alkyl, alkylthio, nitro, nitrile, hydroxy, alkoxy, alkylsulfinyl, alkylsulfonyl, trifluoromethyl or trifluromethoxy;

V is —CH$_2$—;

W is selected from the group consisting of O, S NH and N(alkyl);

Z is selected from the group consisting of NH, N(alkyl), S and O;

$R^1$ is hydrogen, alkyl, allyl, cycloalkyl or cycloalkyl (alkyl);

$R^2$ is hydrogen or 1 to 4 substituents which can be the same or different, each $R^2$ being independently selected from the group consisting of halogen, alkyl, alkylthio, alkylsulfonyl, hydroxy, alkoxy, trifluoromethyl, trifluoromethoxy, aryl, —CH=O, —NO$_2$, —NR$^{11}$R$^{12}$, CN, $R^{10}$-substituted aryl, heteroaryl, —C(O)OR$^8$, —C(O)NR$^3$R$^4$, —S(O)$_2$NR$^3$R$^4$, —C(R$^7$R$^8$)NR$^5$R$^6$, —C(R$^7$)=NOR$^4$ and —C(R$^7$R$^8$)OR$^6$;

$R^3$ is aryl, $R^{10}$-substituted aryl, arylalkyl, heteroaryl, alkyl or hydrogen;

$R^4$ is aryl, $R^{10}$-substituted aryl, heteroaryl, alkyl or hydrogen, or $R^3$, $R^4$ and N of —NR$^3$R$^4$ together can be joined together to form a ring selected from the group consisting of azetidine, $R^8$-substituted azetidine, pyrrolidine, $R^8$-substituted pyrrolidine, piperidine, $R^8$-substituted piperidine, piperazine, $R^8$-substituted piperazine, morpholine and $R^8$-substituted morpholine;

$R^5$ is alkyl, arylalkyl, —C(O)NR$^3$R$^4$, —S(O)$_2$NR$^3$R$^4$, —S(O)$_2$R$^8$, —C(O)R$^8$, —C(O)OR$^8$ or —R$^9$O-alkyl;

$R^6$ is hydrogen, alkyl, aryl, $R^{10}$-substituted aryl, heteroaryl or arylalkyl, or $R^5$, $R^6$ and N in —NR$^5$R$^6$ together can be joined together to form a ring selected from the group consisting of azetidine, $R^8$-substituted azetidine, pyrrolidine, $R^8$-substituted pyrrolidine, piperidine, $R^8$-substituted piperidine, piperazine, $R^8$-substituted piperazine, morpholine and $R^8$-substituted morpholine;

$R^7$ is hydrogen, alkyl, aryl or arylalkyl;

$R^8$ is hydrogen, aryl, alkyl, arylalkyl or heteroaryl;

$R^9$ is hydrogen, alkyl, aryl, $R^{10}$-substituted aryl, heteroaryl or arylalkyl;

$R^{10}$ is selected from the group consisting of aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ may be the same or different and are independently selected from the group consisting of hydrogen, alkyl, aryl, and aralkyl;

$R^{11}$ is hydrogen, alkyl or arylalkyl;

$R^{12}$ is —C(O)R$^{13}$, —S(O)$_2$R$^{13}$, —C(O)NR$^3$R$^4$ or —C(O)OR$^{13}$; and $R^{13}$ is alkyl, aryl, $R^{10}$-substituted aryl, heteroaryl or arylalkyl.

2. The compound of claim 1 wherein
G is halo;
$R^1$ is hydrogen, alkyl, cyclopropyl or cyclopropylmethyl;
$R^2$ is hydrogen; and
W is S or O.

3. The compound of claim 1 wherein G is chloro.

4. The compound of claim 1 wherein $R^1$ is hydrogen or methyl.

5. The compound of claim 1 selected from the group consisting of

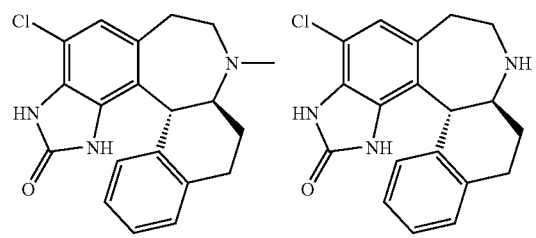

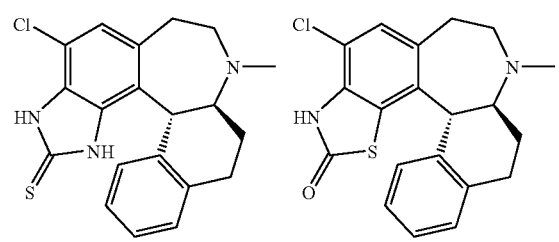

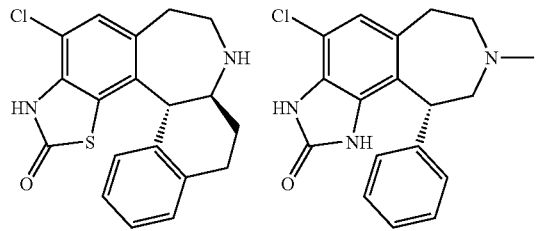

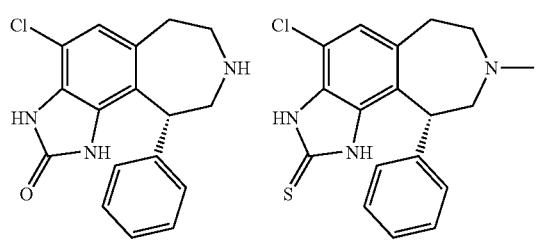

-continued

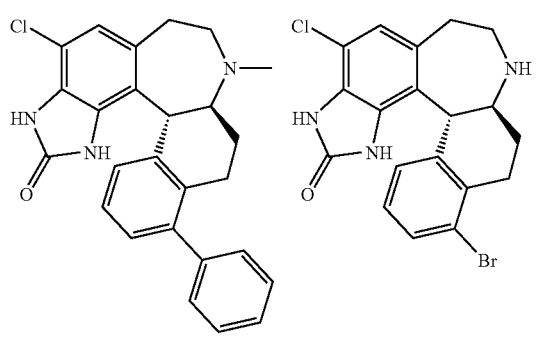

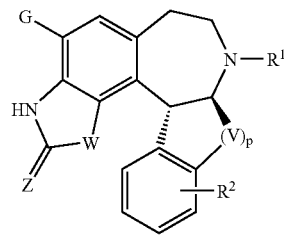

or a pharmaceutically acceptable salt or solvate thereof.

7. A method of treating a metabolic disorder, an eating disorder or diabetes comprising administering to a patient a therapeutically effective amount of at least one compound of claim 1 to a patient in need of such treatment.

8. A method of treating a metabolic disorder, an eating disorder or diabetes comprising administering to a patient a therapeutically effective amount of at least one compound of claim 5 to a patient in need of such treatment.

9. The method of claim 7 wherein said eating disorder is hyperphagia.

10. The method of claim 7 wherein said metabolic disorder is obesity.

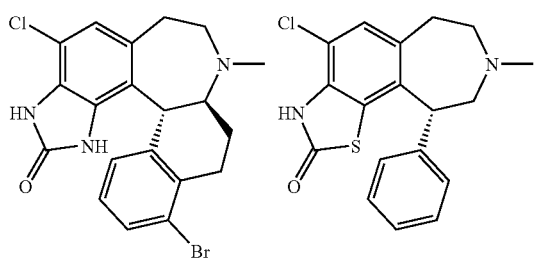 and

11. A method for treating a human afflicted with a disorder selected from the group consisting of obsessive-compulsive disorder, somatoform disorders, dissociative disorders, eating disorders, impulse control disorders, trichotillomania and autism, said method comprising administering an effective amount of the compound of claim 1.

12. The method of claim 11, wherein the eating disorders are selected from the group consisting of anorexia nervosa, bulimia, and binge eating.

13. The method for treating a human afflicted with a disorder of claim 11, wherein the disorder is an impulse control disorder from the group consisting of pathological gambling, compulsive buying, and sexual compulsion.

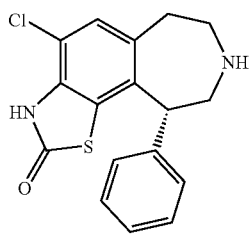

14. A pharmaceutical composition comprising a therapeutically effective amount of at least one compound of claim 1 in combination with at least one pharmaceutically acceptable carrier.

15. A pharmaceutical composition comprising a therapeutically effective amount of at least one compound of claim 5 in combination with at least one pharmaceutically acceptable carrier.

or a pharmaceutically acceptable salt or solvate thereof.

6. A compound of claim 1 having the absolute stereochemistry as shown in the formula 16. A process for making a pharmaceutical composition comprising combining at least one compound of claim 1, and at least one pharmaceutically acceptable carrier.

* * * * *